United States Patent [19]

Davenport

[11] Patent Number: 4,692,546

[45] Date of Patent: * Sep. 8, 1987

[54] PROCESS FOR PRODUCING ACYLOXY AROMATIC CARBOXYLIC ACIDS

[75] Inventor: Kenneth G. Davenport, Corpus Christi, Tex.

[73] Assignee: Celanese Corporation, New York, N.Y.

[*] Notice: The portion of the term of this patent subsequent to May 12, 2004 has been disclaimed.

[21] Appl. No.: 779,893

[22] Filed: Sep. 25, 1985

Related U.S. Application Data

[63] Continuation-in-part of Ser. No. 633,832, Jul. 24, 1984, abandoned.

[51] Int. Cl.$^4$ .................... C07B 41/08; C07C 51/245; C07C 59/52; C07C 69/017
[52] U.S. Cl. ................................ 560/130; 260/406; 560/138; 560/139; 560/141; 560/142; 560/143; 560/144; 562/421; 562/475
[58] Field of Search ................ 562/421, 475; 560/138, 560/139, 141, 130

[56] References Cited

U.S. PATENT DOCUMENTS

| | | | |
|---|---|---|---|
| 2,673,217 | 3/1954 | Hull | 562/421 X |
| 2,833,825 | 5/1958 | Lewis | 568/310 |
| 2,952,703 | 9/1960 | McKeever et al. | 562/421 |
| 3,539,592 | 11/1970 | Crowther et al. | 562/421 X |

OTHER PUBLICATIONS

Dann et al., Annalen der Chemie, 587 Band, pp. 1–15 (1954).
Den Hertog et al., Journal of Catalysis, vol. 6, pp. 357–361 (1966).
Khandual et al., Chemical Abstracts, vol. 77, Abstract No. 125628g (1972).
Simons et al., Journal of the American Chemical Society, vol. 61, pp. 1795–1796 (1939).
Simons et al., Journal of the American Chemical Society, vol. 62, pp. 485–486 (1940).
Van Helden et al., Rec. Trav. Chim., vol. 80, pp. 57–81 (1961).

Primary Examiner—Donald B. Moyer
Assistant Examiner—Patricia M. Scott
Attorney, Agent, or Firm—M. Turken; D. R. Cassady

[57] ABSTRACT

Acyloxy aromatic carboxylic acids, e.g., 4-acetoxybenzoic acid, are prepared by oxidizing with oxygen an acyloxy aromatic ketone, e.g., 4-acetoxyacetophenone in the presence of manganese cations and a lower-carboxylic acid anhydride as catalyst and a co-reductant or promoter. The acyloxy aromatic ketone may be prepared by acylating a hydroxy aromatic ketone, e.g., 4-hydroxyacetophenone, which has the effect of "masking" the hydroxyl group of the ketone in a manner necessary to effect the subsequent transition-metal catalyzed oxidation of the ketone to the acyloxy aromatic carboxylic acid.

9 Claims, No Drawings

PROCESS FOR PRODUCING ACYLOXY AROMATIC CARBOXYLIC ACIDS

This application is a continuation-in-part of application Ser. No. 633,832, filed July 24, 1984, now abandoned.

This invention relates to the catalytic oxidation of acyloxy aromatic ketones to acyloxy aromatic carboxylic acids, e.g., 4-acetoxyacetophenone to 4-acetoxybenzoic acid.

BACKGROUND OF THE INVENTION

It is known to prepare acyloxy aromatic carboxylic acids, e.g., 4-acetoxybenzoic acid (4-ABA), by reacting a phenolic compound, e.g., phenol, with an alkali metal hydroxide, e.g., potassium hydroxide, to form the alkali metal salt of the phenolic compound, e.g., potassium phenoxide, and reacting the salt with carbon dioxide in a Kolbe-Schmitt reaction followed by acidic work-up to form a hydroxy aromatic acid, e.g., 4-hydroxybenzoic acid (4-HBA). The acid is then acylated with an acylating agent, e.g., acetic anhydride, to form the acyloxy aromatic carboxylic acid, e.g., 4-ABA. A substantial disadvantage of this process is the necessity to neutralize the hydroxy aromatic carboxylate salt resulting in the formation of an alkali metal salt which must be separated and disposed of.

The preparation of hydroxy aromatic ketones by the Fries rearrangement of aromatic esters is well-known in the art. Thus, Lewis, U.S. Pat. No. 2,833,825 shows the rearrangement of phenyl or other aromatic esters to acylphenols or other hydroxy aromatic ketones using anhydrous hydrogen fluoride as catalyst. The examples of this patent are limited to the rearrangement of esters of higher fatty acids with the yields ranging from 55 to 95%.

Simons et al., *Journal of the American Chemical Society*, 62, 485 and 486 (1940), show the use of hydrogen fluoride as a condensing agent for various rearrangements and at page 486 show the Fries rearrangement of phenyl acetate to obtain p- hydroxyacetophenone.

Dann and Mylius in a dissertation included as part of a series of Reports from the Institute for Applied Chemistry of the University of Erlangen, *Annalen der Chemie*, 587, 1 to 15, (1954) show the rearrangement of phenyl acetate in hydrogen fluoride to 4-hydroxyacetophenone, with a maximum yield of 81% after 24 hours of reaction time, and report a yield of 92% stated to be obtained by K. Weichert as reported in *Angewandte Chemie*, 56, 338 (1943). However, Dann and Mylius suggest that the difference in yields may be at least partly due to the previous ignoring by Weichert of the accompanying 2-hydroxyacetophenone. Dann and Mylius also report somewhat lower yields of hydroxy aromatic ketones from rearrangements in hydrogen fluoride of acresol acetate, p-cresol acetate, and guaiacol acetate.

Dann and Mylius also disclose the reaction of phenol and glacial acetic acid in the presence of hydrogen fluoride to produce 4-hydroxyacetophenone in a yield of 61.6%. This reaction may be conventionally characterized as a Friedel-Crafts acetylation of phenol with acetic acid as the acetylating agent.

Simons et al., *Journal of the American Chemical Society*, 61, 1795 and 1796 (1939), teach the acylation of aromatic compounds using hydrogen fluoride as a condensing agent and in Table 1 on page 1796 show the acetylation of phenol with acetic acid to produce p-hydroxyacetophenone in 40% yield.

Meussdoerffer et al., German Offenlegungsschrift No. 26 16 986 published Oct. 27, 1977 and assigned to Bayer AG, disclose the acylation of phenolic compounds such as phenol itself wth an acyl halide such as acetyl chloride to form hydroxy aromatic ketones.

Khandual et al., *J. Indian Chem. Soc.*, 49, 557–560 (Eng.) (1972), as abstracted in *C.A.* (1972), 77, 125628g, show the oxidation of acetophenone in 95% acetic acid by manganic acetate to form benzoic acid, and formaldehyde. The oxidation of acetophenone containing ring substituents, e.g., methoxy, is also taught.

Den Hertog et al., *Journal of Catalysis*, 6, 357–361, (1966), show the manganic acetate catalyzed oxidation of acetophenone and acetophenone containing any various ring substituents such as methyl to benzoic acid and corresponding ring substituted benzoic acids.

Van Helden et al., *Rec. Trav. Chim.*, 80, 57–81,(1961), show the manganese ion-catalyzed oxidations of acetophenone and various ring-substituted acetophenones to the corresponding benzoic acids and the cobalt ion-catalyzed oxidation of acetophenone to benzoic acid.

Misra et al., *J. Indian Chem. Soc.*, 52, 1053–1055 (Eng.) (1975) as abstracted in C.A. (1976), 84, 150041n, show the vanadius catalyzed oxidation of acetophenone and acetophenones containing any of various ring substituents such methoxy.

Nippon Kayaku Co., Ltd. (inventors Susumu Nagao and Toshio Takahashi), Japanese Kokai No. Sho 54(1979) - 109941, discloses and claims the oxidation of esters of m-cresol with oxygen in the presence of a heavy metal salt in a solvent of a low molecular weight fatty acid and/or anhydride. It is clear from the published application that the presence of the acid anhydride was not critical to the reaction.

McKeever and Freimiller, U.S. Pat. No. 2,952,703, teaches the oxidation of acetophenone to benzoic acid with oxygen in the presence of a manganese salt, a carboxylic acid, and nitric acid of from 80°–107° C.

Hull, U.S. Pat. No. 2,673,217, teaches the use of aldehydes as co-reductants in the oxidation reaction.

Crowther et al., U.S. Pat. No. 3,539,592, teach the use of a co-reductant, as for example an aldehyde, in the substantial absence of metal catalyst.

Other references pertinent to the oxidation of alkyl and acyl side chains to an acid moiety include:

Kato et al., Japanese Patent No. 75 35,066 issued Nov. 13, 1975, as abstracted in *C.A.* (1976), 85, 5360g; Kobayashi et al., Japanese Patent No. 67 849, issued Jan. 18, 1967, and abstracted in C.A. (1967), 66, 55236Z; and Sangaiah et al., *Synthesis*, 12, 1018–1019, (1980), all show the transition metal-catalyzed oxidation of p-cresyl acetate to 4-acetoxybenzoic acid; and Aoyama et al., Japanese Patent No. 76 108030, discloses the oxidation of 5-acyloxy-meta-xylene to 5-hydroxyisophthalic acid.

SUMMARY OF THE INVENTION

In accordance with this invention, an acyloxy aromatic ketone, e.g., 4-acetoxyacetophenone (4-AAP) is oxidized with oxygen in the presence of transition metal ions and a coreductant and/or promoter and a lower-alkylcarboxylic acid anhydride to produce the corresponding acyloxy aromatic carboxylic acid, e.g., 4-acetoxybenzoic acid (4-ABA). This compound may be used as is or may be hydrolyzed in acid solution to the corresponding hydroxy aromatic carboxylic acid, e.g., 4-hydroxybenzoic acid (4-HBA).

The oxidation reaction proceeds as indicated in equation (I).

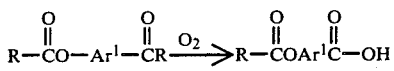 (I)

where R is a monovalent organic radical and Ar¹ is a divalent aromatic radical as will be more specifically defined below.

If 4-acetoxybenzoic acid is the desired product with 4acetoxyacetophenone (4-AAP) as the starting material, the reaction proceeds as in equation (II):

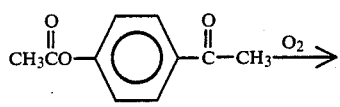 (II)

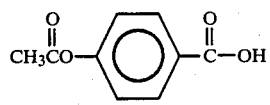

The aromatic ketone which is subsequently oxidized to the acyloxy aromatic carboxylic acid may be produced from a hydroxy aromatic ketone such as 4-hydroxy acetophenone (4-HAP) by first acylating the hydroxy radical of the ketone with an acylating agent such as an acid anhydride to produce the acyloxy aromatic ketone, e.g., 4-acetoxyacetophenone, which is then oxidized with oxygen or an oxygen containing mixture, i.e., air, under the hereinbelow defined conditions to produce the corresponding acyloxy aromatic carboxylic acid, e.g., 4-acetoxybenzoic acid; this can then be hydrolyzed to produce the hydroxy aromatic carboxylic acid, e.g., 4-hydroxybenzoic acid. The acylation of the hydroxy radical of the hydroxy aromatic ketone has the effect of 'masking' the hydroxy radical in a manner necessary to effect the subsequent transition metal-catalyzed oxidation of the ketone group to produce the acyloxy aromatic carboxylic acid in accordance with the invention.

The formation of the acyloxy aromatic ketone from the hydroxy aromatic ketone proceeds as in equation (III):

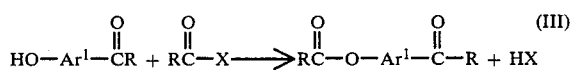 (III)

where Ar¹ is a divalent aromatic radical, R is an alkyl radical and X is the residue of an acylating agent as more fully defined below.

Where it is desired to produce 4-acetoxyacetophenone (4AAP) from 4-hydroxyacetophenone (4-HAP) using acetic anhydride as the acetylating agent, the reaction proceeds as in equation (IV):

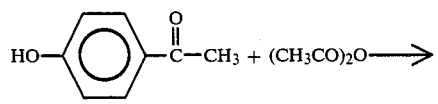 (IV)

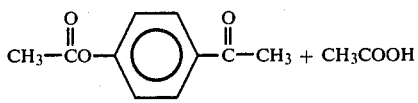

As used in this iinvention, Ar¹ is a divalent monocyclic or bicyclic aromatic hydrocarbon radical. Ar 1 is preferably a radical resulting from the removal of two ring hydrogen atoms from benzene, naphthalene, or biphenyl, either unsubstituted or with ring hydrogens substituted with radicals such as alkyl, alkoxy, or acyloxy containing 1 to 18 carbon atoms; aryl; and appropriately masked hydroxy, amino, or sulfhydryl substituents. Thus, Ar¹ is preferably 1,4phenylene, 2,1-naphthylene, 2,6-naphthylene, 5-phenyl-1,2phenylene, 3-phenyl-1,4,-phenylene or 3-methyl-1,4-phenylene with the ketocarbon and corresponding groups occupying the first stated numbered position of Ar¹ when the positions are not equivalent. Most preferably Ar¹ is 1,4-phenylene.

When Ar¹ is substituted with alkyl, such alkyl substituents may be, for example, substituents as methyl, ethyl, isopropyl, hexyl, decyl, and the like. Two adjacent hydrogen atoms of Ar¹ also may be substituted with the same alkyl chain to form a ring structure.

When Ar¹ is substituted with alkoxy, such alkoxy substituents may be, for example, methoxy, ethoxy, propoxy, and the like. Two adjacent hydrogen atoms on the Ar¹ moiety also may be substituted by the same alkoxy substituent, one through the oxygen atom and one through a carbon atom not adjacent to the oxygen atom to form a ring structure.

When Ar¹ is substituted with an acyloxy moiety, such acyloxy moiety may be, for example, acetoxy, propionoxy, butyroxy, and the like.

When Ar¹ is substituted with aryl, such aryl substituents may be the same as Ar herein below defined.

The R group in equations (I) and (III) may be the same or different and is an alkyl group containing, for example 1 to 18 carbon atoms, preferably 1 to 4 carbon atoms. More preferably, R is the same in all occurrences in equations (I) and (III) and is methyl, ethyl or propyl and most preferably methyl corresponding to the use of acetate esters and methyl ketones in the latter equations. The preferred product is 4-acetoxybenzoic acid (4-ABA) formed by the oxidation of 4-acetoxyacetophenone (4-AAP) which is in turn formed by the acetylation of 4-hydroxyacetophenone (4-HAP).

The hydroxy aromatic ketone used to form the acyloxy aromatic ketone may be prepared by any method known in the art. For example, it may be prepared by the Fries rearrangement of the corresponding aromatic ester as indicated by equation (V) where Arl and R have the definitions given above and Ar is an aryl radical corresponding to the definition of Arl given above except that the carbon bonded to a hydroxy or acyloxy group is bonded to a hydrogen instead.

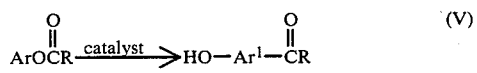 (V)

Alternatively, a phenolic compound and an acylating agent may be reacted in a Friedel-Crafts acylation to form the hydroxy aromatic ketone, in accordance with the following equation:

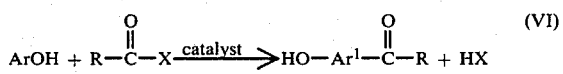

where Ar, Ar¹ and R have the meanings given previously and X in equation (III) and (VI) is the residue minus the acyl group,

of the compounds which are known acylating agents, such as hydroxy; acyloxy, e.g., acetoxy; and halide, e.g., fluoride, chloride, and bromide. Examples of phenolic compounds which may be employed are phenol, 1-naphthol, 2-naphthol, 2-phenylphenol, 4-phenylphenol and o-cresol. Acylating agents which may be used are for example alkanoic acids, e.g., acetic and propionic acids, alkanoic acid anhydrides, e.g., acetic and propionic anhydrides, and acyl halides, e.g., acetyl and propionyl fluorides, chlorides, and bromides. Note that although the reaction of a phenolic compound and an acylating agent is characterized herein as a 'Friedel-Crafts acylation,' no opinion as to the mechanism of reaction should be implied by this characterization.

The catalyst for both of the foregoing reactions is preferably hydrogen fluoride but any other catalyst known in the art to be effective for the Fries and Friedel-Crafts reactions may be used, e.g., aluminum chloride, zinc chloride, or boron trifluoride.

In carrying out the reaction, the aromatic ester or phenolic compound and acylating agent, catalyst, and if desired when an aromatic ester is the starting material, an additive for the reaction such as acetic anhydride or acetic acid, may be charged to a corrosion-resistant reactor and the mixture maintained at a temperature, for example, of about 20 to about 150° C. for a period, for example, of about ½ to about 4 hours, at a pressure, for example, of about 25 to 500 psig. If HF is used as the catalyst, it may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 75 moles per mole of aromatic ester or phenolic compound initially present in the reaction zone. If 4-ABA is the desired product of the reaction, the starting material if a Fries rearrangement is employed will be a phenyl carboxylate, preferably phenyl acetate, while phenol and an acylating agent, preferably an acetylating agent such as acetic acid or acetic anhydride is the starting material if a Friedel-Crafts acylation is utilized. In both cases, the starting material is converted to a 4-hydroxyphenyl ketone such as 4-HAP which is in turn converted by the process of this invention to 4-ABA.

The acyloxy aromatic carboxylic acid product of equation (I) may be hydrolyzed or transesterified to hydroxy aromatic carboxylic acids as shown in equation (VII):

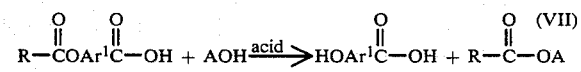

where Ar¹ and R have the definitions given previously, and A is lower alkyl, aryl, or hydrogen.

If the product produced by the process is 4-ABA, and it is desired to hydrolyze such 4-ABA to 4-hydroxybenzoic acid (4-HBA), the reaction proceeds as in equation (VIII):

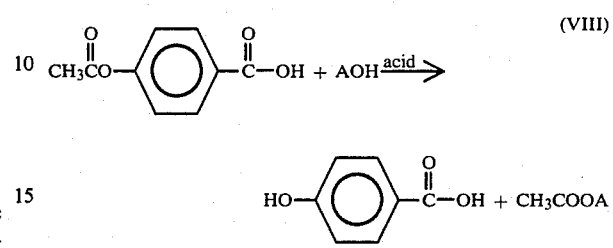

An acyloxy aromatic ketone is oxidized to an acyloxy aromatic acid as indicated by equation (I) by subjecting the ketone to a catalytic oxidation with oxygen.

I have found that the reaction is not so general as one would expect in reviewing the prior art cited above. I have found that a lower-alkyl carboxylic acid anhydride is necessary for the reaction to proceed. I have also found that a concentration ratio of anhydride to ketone of from about 0.5:1 to about 5:1 is preferred and that the best conversion to acid with minimal impurities occurs when the anhydride to ketone concentration ratio is from about 1:1 to about 3:1.

Further, I have found that a soluble salt of the manganese cation must be present in the reaction. Other metal cations commonly known as transition element cations may also be present. The transition element cations particularly useful for the process of this invention are the cations of cobalt, chromium, iron, vanadium, tungsten, and molybdenum.

The convenient anion useful to form a soluble salt of these cations is the anion form of the carboxylic acid used as a solvent for the present reaction.

Although it is possible to carry out the procedure of the present invention in the absence of a solvent, the preferred method is to use a lower alkyl carboxylic acid solvent. It is most convenient to use the same carbon skeleton for the acyloxy function on the ketone, the loweralkyl carboxylic acid solvent, the lower alkyl carboxylic acid anhydride, and the anion moiety of the catalyst salt.

Thus, in the manufacture of 4-acetoxybenzoic acid it is convenient to use acetic acid as a solvent, acetic anhydride as the lower alkyl carboxylic acid anhydride and manganese acetate as the catalyst.

I have found that either a co-reductant or a promoter is necessary to maintain the reaction. The term co-reductant is used to denote a material which is capable of being oxidized along with the desired reactant. If the concentration of the acyloxy aromatic ketone is sufficiently high, >25%, in a solvent-diluted reaction, the compound acts as its own coreductant. As the oxidation proceeds, however, and the concentration is reduced, it has been found necessary to add another material to the reaction mixture to maintain an efficient oxidation rate.

Useful co-reductants are such compounds as lower alkyl aldehydes and dilower alkyl ketones; as for example, acetaldehyde, propionaldehyde, butyraldehyde, acetone, methyl ethyl ketone, diethyl ketone, methyl isopropyl ketone, and the like.

The term promoter is used to denote a salt which acts as a free radical transfer agent. Of particular use are the salts of bromide anion, i.e., ammonium bromide and the alkali metal bromides: lithium bromide, sodium bromide, and potassium bromide.

According to the teaching of this invention, the oxidation can occur in the presence of (1) a sufficiently high concentration of the acyloxy aromatic ketone, (2) added co-reductant, (3) added promoter, (4) 1 (above) then 2 (above), (5) 2 (above) and 3(above), or (6) 1 (above) and 3 (above) then 2 (above).

Oxygen or an oxygen-containing gas is fed into the reaction preferably at such a rate that the amount of oxygen in the vent gas from the reactor does not exceed the level at below which a flammable mixture is attained.

The reaction may be carried out by agitating the reaction mixture at a temperature, for example, of about 90 to about 225° C., preferably about 125 to 175° C., at a pressure, for example, of about 100 to 2000 psig, preferably about 200 to 800 psig, for a period, for example, of about 0.5 to 10 hours, preferably 1 to 4 hours. The catalyst may be used in an amount, for example, of about 1 to 5000 ppm based on the total reaction mass, preferably about 50 to 2000 ppm, the coreductant, if used, in an amount, for example of about 5 to 100 mole percent, preferably about 20 to 50 mole percent based on the acyloxy aromatic ketone, and the promoter, if used, in an amount, for example of about 0.01 to 10 mole % preferably about 0.1 to 1 mole % also based on acyloxy aromatic ketone. The oxygen is added in a manner, as by adequate sparging, to effect a high degree of contact with and mass transfer to the liquid reaction mixture.

In general, the reaction can be carried out to a high conversion of the ketone, e.g., 4.acetoxyacetophenone to all products with a selectivity to the desired acyloxy aromatic carboxylic acid, e.g., 4-acetoxybenzoic acid, of at least 50%.

The acyloxy aromtic carboxylic acids produced by the process of this invention may be used as such or they may be hydrolyzed to the corresponding hydroxy aromatic carboxylic acid as indicated by equation (VII), e.g., by refluxing with an aqueous strong acid such as sulfuric acid.

The acyloxy aromatic ketone used as a starting material for the catalytic oxidation to an acyloxy aromatic carboxylic acid may be obtained as a co-product with the hydroxy aromatic ketone produced by the Fries rearrangement of an aromatic ester or the Friedel-Crafts acetylation of phenol, e.g., when the reaction is carried out in the presence of HF and an acid anhydride. Alternatively, the acyloxy aromatic ketone may be produced from the hydroxy aromatic ketone by reacting the latter with an acylating agent such as an acid anhydride, as indicated by equation (III), by contacting the ketone with, for example, about 1 to 5 moles of the anhydride per mole of ketone at a temperature, for example, in the range of 120 to 140° C. for a period, for example, in the range of ½ to 4 hours.

DESCRIPTION OF SPECIFIC EMBODIMENTS

The following examples further illustrate the invention.

EXAMPLE 1

This example illustrates the preparation of 4-hydroxyacetophenone by the Fries rearrangement of phenyl acetate using hydrogen fluoride as catalyst.

To a 300 cc Hastelloy C autoclave was charged 40.8 g (0.3 mol) of phenyl acetate. The autoclave was sealed, immersed in a dry ice/isopropanol bath and cooled internally to −45° C., and evacuated to ca. 150 Torr. Addition of 120 g (6.0 mol) of anhydrous hydrogen fluoride was performed in a manner such that the internal temperature of the autoclave did not exceed 0° C. The internal pressure of the reactor was then adjusted to 0 psig with nitrogen. The contents of the autoclave were stirred and heated to 75° C. for 1 h. The hydrogen fluoride was vented over a 45 min period at ca. 45° C. The mixture was poured onto 25 g of ice and neutralized with a 45% aqueous solution of potassium hydroxide. The aqueous mixture was extracted with ethyl acetate (3×). The organic fractions were combined and dried over anhydrous magnesium sulfate, filtered, and the solvent was removed on a rotary evaporator to yield 44.0 g of a dark green solid corresponding to 99.9% conversion of phenyl acetate and 94.3% selectivity to 4-hydroxyacetophenone.

EXAMPLE 2

This example illustrates the preparation of 4-hydroxyacetophenone by the Fries rearrangement of phenyl acetate using hydrogen fluoride as catalyst with acetic anhydride as additive.

To a 300 cc Hastelloy C autoclave was charged 30.6 g (0.3 mol) of acetic anhydride. The autoclave was sealed, immersed in a dry ice/isopropanol bath and cooled internally to −50° C., and evacuated to 150 Torr whereupon 120 g (6.0 mol) of anhydrous hydrogen fluoride was transferred from a cylinder to the autoclave. After the transfer of hydrogen fluoride was completed, the internal temperature and the internal pressure of the autoclave was adjusted to −50° C. and 0 psig using nitrogen. To the stirred autoclave was added 81.6 g (0.6 mol) of phenyl acetate at such a rate that the temperature of the mixture did not exceed −23° C. Upon completion of phenyl acetate addition, the contents were warmed to 50° C. and stirred for 3 h during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using a 45% aqueous solution of potassium hydroxide; the mixture was then extracted with 75 ml of ethyl acetate (3×). The organic fractions were combined and dried over anhydrous magnesium sulfate, filtered, and the solvent was removed using a rotary evaporator.

The reaction proceeded with 98.1% conversion of phenyl acetate and with the following selectivities: phenol 1%; 4-hydroxyacetophenone (4-HAP) 82.3%; 2-hydroxyacetophenone (2HAP) 4.3%; 3-hydroxyacetophenone (3-HAP) 0.1%; 4-acetoxyacetophenone (4-AAP) 3.8%; and 4-(4′-hydroxyphenyl)acetophenone (HPAP) 0.4%.

EXAMPLE 3

This example describes the formation of 4-hydroxyacetophenone by the Fries rearrangement of phenyl acetate using hydrogen fluoride as catalyst and acetic acid as additive.

The procedure for Example 2 was repeated except that 18 g (0.3 mol) of acetic acid rather than acetic anhydride were charged to the reactor before it was cooled and charged with the hydrogen fluoride. A conversion of 99.0% of phenyl acetate was obtained with the following selectivities: phenol 3.3%; acetic acid 0.8%; 4-HAP 80.8%; 3-HAP 0; 2-HAP 5.8%; 4-AAP 0.3%; and HPAP 0.3%.

EXAMPLE 4

This example illustrates the preparation of 4-hydroxyacetophenone (4-HAP) by the Friedel-Crafts acetylation of phenol with acetic acid as the acetylating agent.

To a 300 cc Hastelloy C autoclave were charged 9.4 g (0.1 mol) of phenol and 12.0 g (0.2 mol) of acetic acid. The autoclave was sealed, internally cooled to −20° C., and evacuated to 150 Torr, whereupon 100 g (5.0 mol) of anhydrous hydrogen fluoride were transferred from a cylinder to the autoclave. The contents of the autoclave were heated to 80° C. and maintained at that temperature for 1 hour. The contents of the autoclave were then cooled to ca. 20° C. and the hydrogen fluoride was vented to a potassium hydroxide scrubber. Ethyl acetate was added to the contents of the autoclave and the resulting solution was neutralized with a 45% solution of potassium hydroxide. The organic phase was separated, dried over anhydrous magnesium sulfate, and filtered. The solvent was removed on a rotary evaporator to afford 13.1 g (96% yield) of crystalline 4-HAP.

EXAMPLE 5

This example illustrates the preparation of 4-hydroxyacetophenone by the Friedel-Crafts acetylation of phenol with acetic anhydride as the acetylating agent.

To a 300 cc Hastelloy C autoclave cooled to −20° C. and evacuated to 150 Torr was added 150 g (7.5 mole) of anhydrous hydrogen fluoride. The content of the autoclave was warmed to 50° C. resulting in an internal pressure of 25 psig. A solution of 23.5 g (0.25 mol) of phenol and 25.5 g (0.25 mol) of acetic anhydride was added to the autoclave over a 3 minute period causing the pressure to drop to 14 psig. The solution was stirred for 1 h at 50° C. whereupon the hydrogen fluoride was vented at the reaction temperature. The contents of the autoclave were poured onto ice and the aqueous phase was adjusted to pH 6.0 with a 45% solution of potassium hydroxide. The aqueous phase was extracted with 75 mL of ethyl acetate (3×); the organic fractions were combined, dried over anhydrous magnesium sulfate, and filtered. The reaction proceeded with 99% conversion based on phenol and 95% selectivity to 4-hydroxyacetophenone.

EXAMPLE 6

The following example illustrates the reaction of 4-hydroxyacetophenone (4-HAP) with acetic anhydride to form 4-acetoxyacetophenone (4-AAP).

A solution of 136.2 g (1.0 mol) of 4-hydroxyacetophenone and 400 mL of acetic anhydride was heated at reflux for 3 h under a nitrogen atmosphere. The acetic acid and acetic anhydride was distilled overhead in vacuo (39°–41° C., 2.6 mm Hg). The remaining oil was then distilled in vacuo (132°–134 ° C., 2.0 mm Hg) to yield 169.7 g (95.2%) of white crystals identified as 4-acetoxyacetophenone.

Examples 7 to 10 illustrate the oxidation of 4-acetoxyacetophenone (4-AAP) to 4-acetoxybenzoic acid (4-ABA).

EXAMPLE 7

A 300 cc Hastelloy C autoclave was charged with 17.8 g (0.1 mol) of 4-acetoxy acetophenone (4-AAP), 0.25 g of manganese (II) acetate tetrahydrate, 1.0 g of acetaldehyde, 25 g of acetic anhydride, and 125 g of acetic acid. An oxygen/nitrogen mixture was sparged into the autoclave at 1000 cc/min such that 5% oxygen was maintained in the vent. A 10% acetaldehyde in acetic acid solution was fed at a rate of 3.0 cc/h. The reaction was run at 150° C. and 100 psig for 3 h. using a stirring speed of 1000 rpm whereupon the acetic acid and acetic anhydride were removed on a rotary evaporator to yield orange crystals. The crystals were dissolved in ca. 150 mL of ethyl acetate and the solution was extracted with 100 mL of water (3×). The organic phase was dried over anhydrous magnesium sulfate, filtered, and the solvent was removed on a rotary evaporator to yield 4-acetoxybenzoic acid (4-ABA) at a conversion of 92.7% based on 4-HAP and with 55.1% selectivity to 4-ABA.

EXAMPLE 8, 9, 10, 11

Following generally the procedure of Example 7, 4-acetoxyacetophenone was converted to 4-acetoxybenzoic acid. The reactants, conditions, conversions, and selectivities are reported in the following table.

|  | Example 8 | Example 9 | Example 10 | Example 11 |
| --- | --- | --- | --- | --- |
| 4-acetoxyacetophenone (g) | 35.8 | 49.8 | 71.2 | 71.2 |
| Manganese(II) diacetate 4H$_2$O (g) | 2.5 | 1.0 | 2.0 | 1.0 |
| Acetic anhydride (g) | 40.8 | 48.6 | 69.1 | 58.2 |
| Acetic acid (g) | 176.6 | 101.6 | 58.4 | 70.6 |
| Sodium acetate (g) | 0 | 0.35 | 0 | 0 |
| Air (cc/min) | 1000 (a) | 800 (b) | 800 (c) | 800 (d) |
| Oxygen content at vent (%) | <9.5 | <10.5 | <10.6 | <7.5 |
| Temperature °C. | 130 | 130 | 150 | 110 |
| Pressure (psig) | 400 | 400 | 400 | 400 |
| Stirring rate (rpm) | 1000 | 1000 | 1000 | 1000 |
| Reaction time (min) | 108 | 145 | 180 | 210 |
| Conversion (%) | 99.9 | 93.8 | 99.4 | 67.5 |
| Selectivity (%) | 85.0 | 88.3 | 76.0 | 73.4 |

(a) Switched to 500 cc/min air and 500 cc/min N2 after 63 minutes.
(b) Switched to 400 cc/min air and 400 cc/min N2 after 50 minutes.
(c) Switched to 400 cc/min air and 400 cc/min N2 after 90 minutes.
(d) Switched to 400 cc/min air and 400 cc/min N2 after 30 minutes.

The procedures of the examples may also be used to prepare 4-acetoxy-3-methylbenzoic acid from o-cresyl acetate or o-cresol and acetic acid; 1-acetoxy-2-napthoic acid from 1-naphthyl acetate or 1-naphthol and acetic acid; 6-acetoxy2-naphthoic acid from 2-naphthyl acetate or 2-naphthol and acetic acid; 2-acetoxy-5-phenylbenzoic acid from 4-phenylphenyl acetate or 4-phenylphenol and acetic acid; and 4acetoxy.3-phenylbenzoic acid from 2-phenylphenyl acetate or 2-phenylphenol and acetic acid.

The acyloxy aromatic carboxylic acid of this invention, e.g., 4-ABA may be utilized as monomers in the preparation of polymers capable of forming an anisotropic melt phase and suitable for being formed into shaped articles such as molded articles, fibers and films, as shown, for example in U.S. Pat. Nos. 4,339,375; 4,341,688; 4,351,918; and 4,355,132.

The acyloxy aromatic carboxylic acids of this invention, e.g., 4-ABA, may also be hydrolyzed to form the corresponding hydroxy aromatic carboxylic acids, e.g., 4-hydroxybenzoic acid (4-HBA) which has many uses in organic syntheses, and as an intermediate for preservatives, dyes and fungicides. The following example illustrates this process.

EXAMPLE 12

A solution of 4.5 g (0.025 mole) of 4-acetoxybenzoic acid, 25 g of dimethoxyethane, 25 g of water, and 6.1 g of concentrated sulfuric acid was heated at reflux for 2 hours under a nitrogen atmosphere. The solution was cooled, saturated with sodium chloride, and extracted with 75 mL of ethyl acetate (3x). The organic fractions were combined, dried over anhydrous magnesium sulfate, and filtered. Rotary evaporation afforded a substantially quantitative yield of 4-hydroxybenzoic acid based on the 4-acetoxybenzoic acid.

I claim:

1. A process comprising oxidizing an alkyl alkanoyloxy aryl ketone with oxygen in the presence of a soluble salt of the manganese cation, a lower-alkylcarboxylic acid anhydride and a co-reductant or promoter to form an alkanoyloxy aryl carboxylic acid.

2. The process of claim 1 wherein said ketone is 4-acetoxyacetophenone, said lower-alkylcarboxylic acid anhydride is acetic anhydride, said co-reductant is acetaldehyde, and said product is 4-acetoxybenzoic acid.

3. The process of claim 2 wherein said 4-acetoxybenzoic acid is hydrolyzed to 4-hydroxybenzoic acid.

4. A process comprising reacting an alkyl hydroxy aryl ketone with a lower-alkylcarboxylic acid anhydride to form an alkyl lower-alkanoyloxy aryl ketone, and oxidizing said alkyl alkanoyloxy aryl ketone with oxygen in the presence of a soluble salt of the manganese cation, a lower-alkylcarboxylic acid anhydride and a co-reductant or promoter to form a lower-alkanoyloxy aryl carboxylic acid.

5. The process of claim 4 wherein the said alkyl hydroxy aryl ketone is 4-hydroxyacetophenone, said lower-alkylcarboxylic acid anhydride is acetic anhydride, said alkyl lower-alkanoyloxyaryl ketone is 4-acetoxyacetophenone, and said lower-alkanoyloxy aryl carboxylic acid is 4-acetoxybenzoic acid.

6. A process comprising contacting a lower-alkanoyloxy aryl compound and a lower-alkylcarboxylic acid with a Fries rearrangement catalyst to form an alkyl hydroxy aryl ketone, reacting said hydroxy aryl ketone with a lower-alkylcarboxylic acid anhydride to form an alkyl lower-alkanoyloxy aryl ketone, and oxidizing said alkyl lower-alkanoyloxy aryl ketone with oxygen in the presence of a soluble salt of the manganese cation, lower-alkylcarboxylic acid anhydride, and a co-reductant or promotor to form a lower-alkanoyloxy aryl carboxylic acid.

7. The process of claim 6 wherein said Fries rearrangement catalyst is hydrogen fluoride.

8. A process comprising contacting a phenolic compound and an acylating agent selected from the group consisting of alkanoic acid, alkanoic acid ahhydride and alkanoic acid halide with a Friedel-Crafts catalyst to form an alkyl hydroxy aryl ketone, reacting said alkyl hydroxy aryl ketone with a lower-alkylcarboxylic acid anydride to form an alkyl lower-alkanoyloxy aryl ketone, and oxidizing said alkyl lower-alkanoyloxy aryl ketone with oxygen in the presence of a soluble salt of the manganese cation, a lower-alkylcarboxylic acid anhydride and a co-reductant or promoter to form a lower-alkanoyloxy aryl carboxylic acid.

9. The process of claim 8 where said Friedel-Crafts catalyst is hydrogen fluroide.

* * * * *